United States Patent
Thul et al.

(10) Patent No.: US 10,488,327 B2
(45) Date of Patent: Nov. 26, 2019

(54) TEMPERATURE PROFILE FOR ROCK SAMPLE COMPOSITION ANALYSIS

(71) Applicant: UNIVERSITY OF UTAH RESEARCH FOUNDATION, Salt Lake City, UT (US)

(72) Inventors: David J. Thul, Salt Lake City, UT (US); Dhrupad Raghuveer Beti, Salt Lake City, UT (US)

(73) Assignee: University of Utah Research Foundation, Salt Lake City, UT (US)

(*) Notice: Subject to any disclaimer, the term of this patent is extended or adjusted under 35 U.S.C. 154(b) by 105 days.

(21) Appl. No.: 15/663,572

(22) Filed: Jul. 28, 2017

(65) Prior Publication Data
US 2018/0031467 A1 Feb. 1, 2018

Related U.S. Application Data

(60) Provisional application No. 62/368,561, filed on Jul. 29, 2016.

(51) Int. Cl.
| | |
|---|---|
| *G01N 21/00* | (2006.01) |
| *G01N 21/17* | (2006.01) |
| *C10B 53/06* | (2006.01) |
| *G06F 17/14* | (2006.01) |
| *G01N 30/02* | (2006.01) |
| *G01N 30/72* | (2006.01) |
| *G01N 1/28* | (2006.01) |

(52) U.S. Cl.
CPC ........ *G01N 21/1717* (2013.01); *C10B 53/06* (2013.01); *G01N 1/28* (2013.01); *G01N 30/02* (2013.01); *G01N 30/72* (2013.01); *G06F 17/14* (2013.01); *G01N 2021/1731* (2013.01); *G01N 2030/025* (2013.01)

(58) Field of Classification Search
CPC .............................................. G01N 2021/1731
See application file for complete search history.

(56) References Cited

U.S. PATENT DOCUMENTS

| | | | | |
|---|---|---|---|---|
| 3,446,597 A | * | 5/1969 | Bray | ................... G01N 33/241 436/32 |
| 9,080,441 B2 | * | 7/2015 | Meurer | ............... E21B 43/2401 |
| 2015/0346179 A1 | * | 12/2015 | Pillot | .................. G01N 33/241 702/2 |

\* cited by examiner

*Primary Examiner* — Lisa M Caputo
*Assistant Examiner* — Alex T Devito
(74) *Attorney, Agent, or Firm* — Workman Nydegger

(57) ABSTRACT

A method for analyzing the petroleum content of a rock sample includes at least three repetitions of heating a rock sample to a holding temperature, holding the rock sample at the holding temperature for a holding period, and collecting data about the rock sample during each holding period. The holding temperature for each subsequent holding period may be greater than or equal to a previous holding temperature. The data collected may be analyzed to determine the S1 parameter and calculated to determine the API gravity of the rock sample.

19 Claims, 8 Drawing Sheets

TEMPERATURE PROFILE FOR ROCK SAMPLE COMPOSITION ANALYSIS

CROSS-REFERENCE TO RELATED APPLICATIONS

This application claims priority to and the benefit of U.S. Provisional Patent Application Ser. No. 62/368,561, filed Jul. 29, 2016 and titled "TEMPERATURE PROFILE FOR ROCK SAMPLE COMPOSITION ANALYSIS," the disclosure of which is incorporated herein by this reference in its entirety.

BACKGROUND

Characterization of oil fields often occurs through the analysis of rock samples removed from the earth during drilling operations. One method of analysis is pyrolysis, in which a rock sample is heated in an inert environment, causing free hydrocarbons and kerogen-based hydrocarbons to decompose. Analyzing the gases released from decomposed hydrocarbons may then help categorize the size and maturity of the oilfield.

At temperatures below 350° C., the gases are released from free hydrocarbons. The amount of free hydrocarbons in the rock sample is called the S1 parameter. The S1 parameter may be determined through pyrolysis heating programs, which may include heating a rock sample for a period of time at a temperature less than 350° C., followed by heating a rock sample for a period of time at a temperature of 300° C. or 350° C.

At temperatures below about 800° C., kerogen in the rock sample is cracked and converted into heavier hydrocarbons. The amount of kerogen-derived hydrocarbons is called the S2 parameter. The S1 and the S2 parameter may be used to help classify the rock and the hydrocarbons contained therein.

The density of oil is often compared to the density of water using the American Petroleum Institute (API) gravity index. A higher API gravity indicates a lower petroleum density. Crude oils with a high API gravity are often more profitable than similarly accessed crude oils with a low API gravity. API gravity of a rock sample is usually determined in a lab by processing the crude oil from a rock sample and comparing it to that of water.

SUMMARY

A method for analyzing the petroleum content of a rock sample includes heating a rock sample to a holding temperature, holding the rock sample at the holding temperature for a holding period, and collecting data on properties of the gases released from the rock sample during heating and holding. The steps of heating, holding, and collecting may be repeated at least three times at a temperature less than 350° C., and in some instances, each holding step occurs at a higher temperature than the previous holding temperature. The results of the foregoing can be used to determine the S1 parameter. Additionally, prior to the first heating step and after the final holding period, the rock sample is analyzed using Fourier transform infrared spectroscopy (FTIR). Additional data are collected about the rock sample using gas chromatography, mass spectrometry, FTIR, or a pyrolysis machine during any of the holding periods. At least a portion of these data and the data from the Fourier transform infrared spectroscopy performed before the first heating step and subsequent to the final holding period are used to calculate the API gravity of the rock sample. The data may be collected in an inert or oxygen-free environment, and to prevent losses, the data may additionally, or alternatively, be collected in a closed system.

A method for analyzing the free petroleum content of a rock sample can include analyzing a rock sample using Fourier transform infrared spectroscopy followed by heating the rock sample from a base temperature to a first holding temperature that is greater than the base temperature. The method can additionally include holding the rock sample at the first holding temperature for a first holding period followed by heating the rock sample to a second holding temperature that is greater than the first holding temperature. The method can further include holding the rock sample at the second holding temperature for a second holding period followed by heating the rock sample to a third holding temperature that is greater than the second holding temperature and no more than 350° C. where the rock sample is held at the third holding temperature for a third holding period. The method can also include collecting data on properties of gases released from the rock sample during any and/or each of the holding periods through at least one of pyrolysis, gas chromatography, and mass spectrometry. Following the third holding period and while the rock sample is at a temperature no more than 350° C., the method can additionally include analyzing the rock sample using Fourier transform infrared spectroscopy followed by heating the rock sample to a fourth holding temperature that is greater than the third holding temperature and no more than 800° C.

Embodiments of the present disclosure additionally include computing systems having one or more processors and one or more hardware storage devices having stored thereon computer-executable instructions that are executable by the one or more processors for causing the computing system to implement a method for analyzing the petroleum content of a rock sample. The method includes receiving data from an analysis of rock sample using Fourier transform infrared spectroscopy, and subsequent to receiving the data from the analysis of the rock sample using Fourier transform infrared spectroscopy, receiving one or more properties of one or more gases released from the rock sample during a first holding period, a second holding period, and a third holding period through at least one of pyrolysis, gas chromatography, and mass spectrometry. Prior to the first holding period, the rock sample is heated from a base temperature to a first holding temperature, the first holding temperature being greater than the base temperature. Subsequent to the first holding period and prior to the second holding period, the rock sample is heated to a second holding temperature, the second holding temperature being greater than the first holding temperature. Subsequent to the second holding period and prior to the third holding period, the rock sample is heated to a third holding temperature, the third holding temperature being greater than the second holding temperature and no more than 350° C. The method further includes receiving data from a subsequent analysis of the rock sample using Fourier transform infrared spectroscopy, subsequent to the third holding period.

A temperature profile, including the holding temperatures and the holding periods, may be implemented in an oven using a computer system. Computer executable instructions may be stored on a hardware storage device. The computer executable instructions may be executed by one or more processors to change the temperature of an oven.

BRIEF DESCRIPTION OF THE DRAWINGS

In order to describe the manner in which the above-recited and other features of the disclosure can be obtained, a more particular description will be rendered by reference to specific embodiments thereof which are illustrated in the appended drawings. For better understanding, the like elements have been designated by like reference numbers throughout the various accompanying Figures. While some of the drawings may be schematic or exaggerated representations of concepts, at least some of the drawings may be drawn to scale. Understanding that the drawings depict some example embodiments, the embodiments will be described and explained with additional specificity and detail through the use of the accompanying drawings in which.

DETAILED DESCRIPTION

Figure 1:
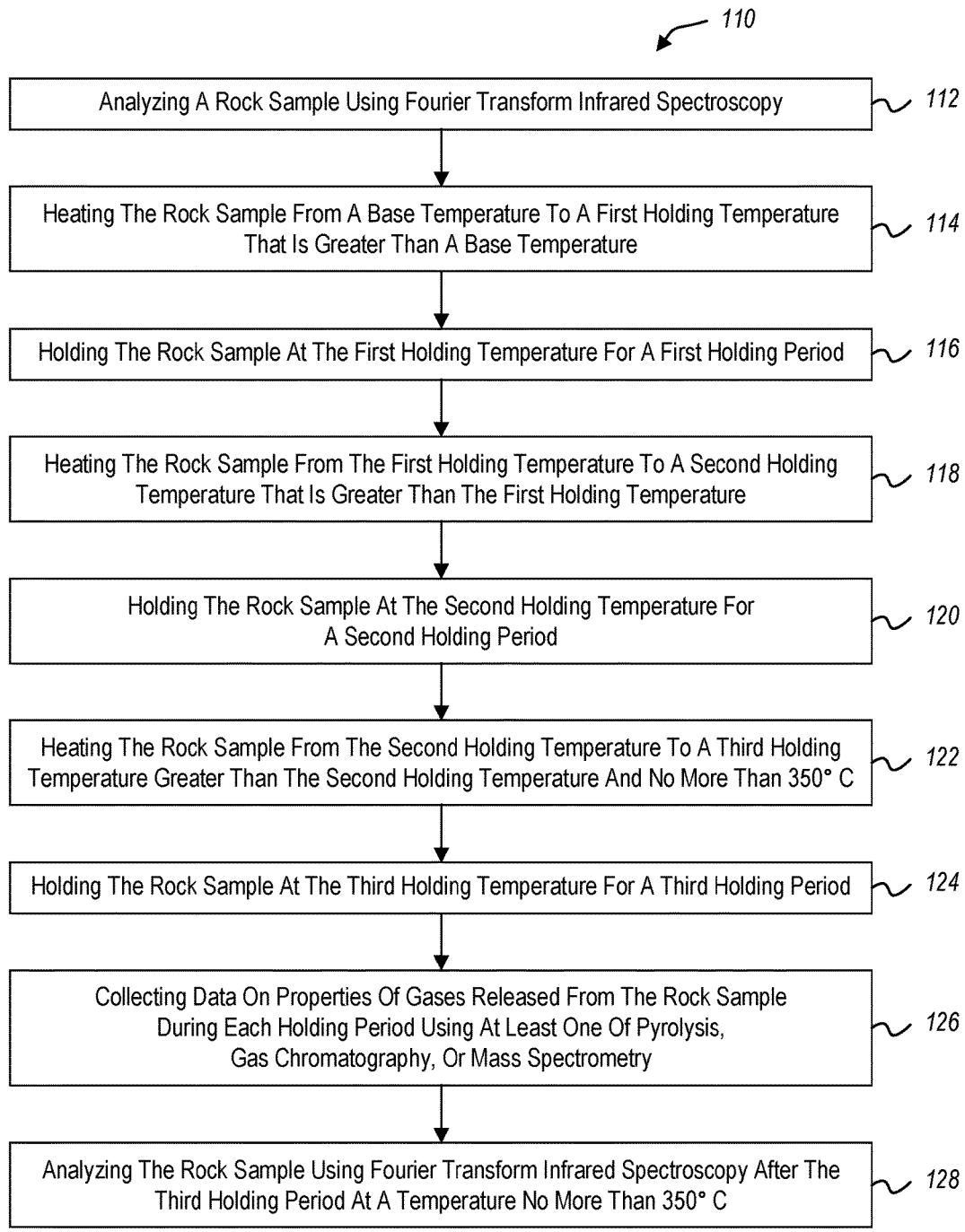
FIG. 1 is a flow chart describing an exemplary method for analyzing the petroleum content of a rock sample.

It is to be understood that the following disclosure provides many different embodiments, or examples, for implementing different features of various embodiments. Specific examples of components and arrangements are described below to simplify the disclosure. These are, of course, merely examples and are not intended to be limiting. In addition, the disclosure may repeat reference numerals and/or letters in the various examples. This repetition is for the purpose of simplicity and clarity and does not in itself dictate a relationship between the various embodiments and/or configurations discussed.

FIG. 1 illustrates a method 110 for analyzing the free petroleum content of a rock sample. The method 110 includes analyzing a rock sample using Fourier transform infrared spectroscopy (FTIR) (act 112); heating the rock sample from a base temperature to a first holding temperature that is greater than the base temperature (act 114); holding the rock sample at the first holding temperature for a first holding (act 116); heating the rock sample from the first holding temperature a second holding temperature it is greater than the first holding temperature (act 118); holding the rock sample at the second holding temperature for a second holding period (act 120); heating the rock sample from the second holding temperature to a third holding temperature greater than the second holding temperature and no more than 350° C. (act 122); holding the rock sample at the third holding temperature for a holding period (act 124); collecting data on properties of gases released from the rock sample during each holding period using at least one of pyrolysis, gas chromatography, or mass spectrometry (act 126); and analyzing the rock sample using FTIR after the third holding period at a temperature no more than 350° C.

In some embodiments, act 112 of analyzing a rock sample using FTIR occurs prior to act 114 of heating the rock sample from a base temperature to a first holding temperature and may allow for an initial reference point for determining the composition of the rock sample. Collecting initial composition information about the rock sample may provide a standard for comparison during later analysis of the rock sample. Additionally, in other embodiments, act 128 of analyzing the rock sample using FTIR after all repetitions of heating (acts 114, 118, and 122), holding (acts 116, 120, and 124), and collecting (act 126) are completed, and at a temperature no more than 350° C., may allow for a final or comparative reference point for determining the composition of the rock sample. Comparison of the results from the two FTIR analyses may provide additional data to help calculate parameters of the rock sample. In some embodiments, act 112 of analyzing by FTIR may be completed after the sample is heated to a temperature roughly corresponding to the S1 peak, or about 350° C. The sample may then be heated (e.g., by acts 114, 118, and 122) to a temperature roughly corresponding to the S2 peak, or about 800° C. where the sample is analyzed by FTIR (act 128) once again.

In some embodiments, the rock sample may be heated from a base temperature to a holding temperature (e.g., as in act 114). In some embodiments, the base temperature may be about 25° C., or ambient or room temperature. In other embodiments, the base temperature may be greater than 25° C. In still other embodiments, the base temperature may be in a range having an upper value, a lower value, or upper and lower values including any of 25°, 50°, 100°, 150°, 200°, 250°, 300°, 350°, or any value therebetween. For example, the base temperature may be greater than 25° C. In another example, the base temperature may be less than 350° C. In yet other examples, the base temperature may be any value in a range between 25° and 350° C. In further examples, the base temperature may be any value in a range between 25° and 330° C. In further examples, the base temperature may be any value in a range between 25° and 300° C.

Heating the rock sample (e.g., as in any of acts 114, 118, and/or 122) may occur at a rate of up to 200° C. per minute. In some embodiments, heating the rock sample may occur at a rate of 50° C. per minute. In other examples, heating the rock sample may occur at a rate in a range having an upper value, a lower value, or upper and lower values including any of 50°, 100°, 150°, 200° C. per minute, or any value therebetween. For example, heating the rock sample may occur at a rate greater than 50° C. per minute. In another example, heating the rock sample may occur at a rate less than 200° C. per minute. In yet other examples, heating the rock sample may occur at any rate in a range between 50° C. per minute and 200° C. per minute.

In some embodiments, a temperature difference between two successive holding temperatures may be greater than 10° C. For example, the temperature difference may be 25° C. In other examples, the temperature difference may be in a range having an upper value, a lower value, or upper and lower values including any of 10°, 50°, 100°, 150°, 200°, 250°, 300°, 350° C., or any value therebetween. For example, the temperature difference may be greater than 10° C. In another example, the temperature difference may be less than 250° C. In yet other examples, the temperature difference may be any value in a range between 10° C. and 350° C. In further examples, the temperature difference may be any value in a range between 10° C. and 250° C. In further examples, the temperature difference may be any value in a range between 10° C. and 150° C.

After the rock sample is heated to the holding temperature, the rock sample is held at the holding temperature for a holding period (e.g., as in any of acts 116, 120, and/or 124). In some embodiments, holding the rock sample may include a holding period of five minutes. In other examples, the holding period may be in a range having an upper value, a lower value, or upper and lower values including any of three, four, five, six, seven, greater than seven minutes, or any value therebetween. For example, the holding period may be greater than three minutes. In another example, the holding period may be less than seven minutes. In yet other examples, the holding period may be any value in a range between three and seven minutes.

Additionally, in some embodiments, a temperature of the rock sample may be held within plus or minus 1° C. during the holding period. In other embodiments, the temperature of the rock sample may be held within plus or minus 0.1° C. In still other embodiments, the temperature of the rock sample may be held within a range having an upper value, a lower value, or upper and lower values including any of 0.1°, 0.25°, 0.5°, 1°, 1.5°, 2°, 5°, 10°, or any value therebetween. For example, the temperature of the rock sample may be held within plus or minus 0.1° C. In another example, the temperature of the rock sample may be held within plus or minus 10° C. In yet other examples, the temperature of the rock sample may be held within a range between 0.1° and 10° C.

Data about properties of the rock sample may be collected while holding the rock sample at the holding temperature (e.g., as recited in act 126 of method 110). Collecting the data may be accomplished using any of one or more techniques, such as pyrolysis, gas chromatography, and/or mass spectrometry. For example, hydrocarbon content may be measured using pyrolysis. Other examples may include the measurement of gases released using gas chromatography. Still more examples may include using mass spectrometry to measure the weight of compounds released during a holding period. In some embodiments, the techniques used to collect may include any one, or any combination of techniques. For example, gas chromatography may be used in conjunction with mass spectrometry. Other examples may include gas chromatography used in conjunction with pyrolysis.

In some embodiments, collecting data about rock properties may help define oilfield parameters. For example, data collected may help determine the S1 parameter, or free hydrocarbon content within a representative rock sample. Other examples include collecting data to help determine the S2 parameter, or the hydrocarbons formed during pyrolysis of kerogen. Still other examples may include the $T_{max}$ parameter, or the temperature at the maximum emission of hydrocarbons from the sample. In some embodiments, the temperature of the sample will be reduced, and the amount of $CO_2$ released during heating may be measured as the S3 parameter. The amount of residual carbon remaining in the sample after the sample is cooled may also be measured as the S4 parameter.

With continued reference to FIG. 1, in some embodiments, the acts of heating (e.g., acts 114, 118, 122), holding (e.g., acts 116, 120, 124), and collecting (e.g., act 126) are performed for a total of at least three holding periods and at least three holding temperatures. For example, the rock sample may be heated from a base temperature to a first holding temperature, the first holding temperature being greater than the base temperature (act 114). The rock sample may be held at the first holding temperature for a first holding period (act 116), whereupon data from the rock sample is collected during the first holding period (act 126). Then, the rock sample may be heated from the first holding temperature to a second holding temperature, the second holding temperature being greater than the first holding temperature (act 118). The rock sample may be held at the second holding temperature for a second holding period (act 120), whereupon data from the rock sample is collected during the second holding period (act 126). The rock sample may then be heated from the second holding temperature to a third holding temperature, the third holding temperature being greater than the second holding temperature (act 122). The rock sample may be held at the third holding temperature for a third holding period (act 124), whereupon data from the rock sample is collected during the third holding period (act 126).

Repeating the steps of heating, holding, and collecting, may help to characterize the detailed composition of the free hydrocarbons of the rock sample, or more clearly define the S1 parameter. For example, a first free hydrocarbon may have a first decomposition temperature, a second free hydrocarbon may have a second decomposition temperature, and a third free hydrocarbon may have a third decomposition temperature. If the first holding temperature is at least the first decomposition temperature, holding the first holding temperature may cause the first free hydrocarbon to decompose. Collecting data about the decomposed first free hydrocarbon may help determine the amount of the first free hydrocarbon present in the rock sample. In like manner, holding the rock sample at a second holding temperature that is at least the second decomposition temperature may decompose the second free hydrocarbon. Collecting data about the decomposed second free hydrocarbon may help define the amount of second free hydrocarbon in the rock sample. Similarly, holding the rock sample at a third holding temperature that is at least the third decomposition temperature may decompose the third free hydrocarbon. Collecting data about the decomposed third free hydrocarbon may help define the amount of third free hydrocarbon in the rock sample. In some embodiments, by choosing each holding temperature to correspond with the decomposition temperature of a free hydrocarbon, a detailed analysis of the free hydrocarbon content of a rock sample may be completed. The S1 parameter may be determined by collecting data at holding temperatures less than about 350° C.; heating, holding, and collecting up to a third holding temperature of 350° C. (as provided by method 110) may provide the information needed to determine the free hydrocarbon content. Additionally, analysis of the data collected may help calculate API gravity in the field without having to process the sample and produce a liquid petroleum product.

The S2 parameter may be defined by repeating the steps of heating (e.g., acts 114, 118, 122), holding (e.g., 116, 120, 124), and collecting (e.g., act 126) at a temperature up to the temperature at which the hydrocarbons stop decomposing, which is typically less than 800° C. In at least one embodiment, the third holding temperature may be 350° C. to define the S1 parameter, and a fourth holding temperature may be less than 800° C. to help define the S2 parameter.

In some embodiments, heating (e.g., acts 114, 118, 122), holding (e.g., 116, 120, 124), and collecting (e.g., act 126) may occur in an inert environment. For example, the inert environment may include a vacuum. Other examples include a non-oxidizing atmosphere, such as an argon, nitrogen, or helium atmosphere. Additionally, in some embodiments, the rock sample may be analyzed in a closed system to prevent the infiltration of contaminants. For example, the closed system may include a sample that is prepared and analyzed in the same container. Other examples may include a sample that is prepared in a vacuum, and any gases and dust released during sample preparation may be transferred to an oven for analysis.

Prior to heating, the sample may be prepared by crushing the sample to a particle size of less than 40 mesh (0.47 mm). The sample preparation method may be similar to the sample preparation method for pyrolysis analysis, known to those with skill in the art.

Figure 2:
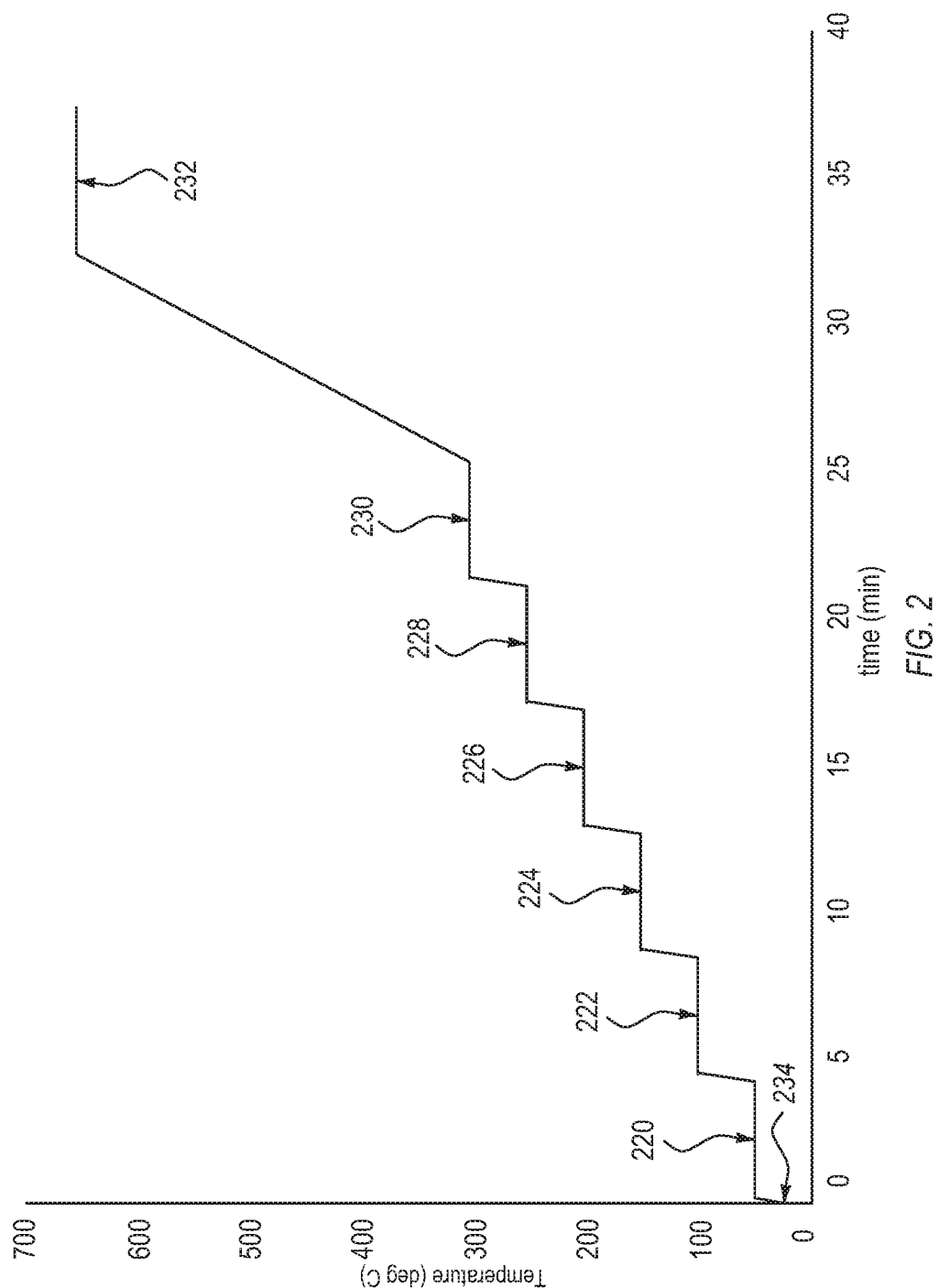
FIG. 2 illustrates an example temperature profile.

In some embodiments, the steps of heating (e.g., acts 114, 118, 122), holding (e.g., 116, 120, 124), and collecting (e.g., act 126) may be repeated more than three times. For example, referring to FIG. 2, analysis of a rock sample may include seven repetitions of heating, holding and collecting, and include seven holding temperatures, 220, 222, 224, 226, 228, 230, 232. In other embodiments, analysis of a rock sample may include any of 3, 4, 5, 6, 7, 8, 9, 10, 11, 12, or more repetitions of heating, holding, and collecting.

Referring back to FIG. 1, the differences in temperature between successive holding temperatures may be the same, but in some embodiments, they may be different. For example, in the method 110, a first difference in temperature (e.g., between the base temperature and the first holding temperature) may be 50° C., a second difference in temperature (e.g., between the first and second holding temperatures) may be 75° C., and a third difference in temperature (e.g., between the second and third holding temperatures) may be 40° C. Additional examples include a first difference in temperature that may be 100° C., a second difference in temperature that may be 30° C., and a third difference in temperature that may be 110° C.

In some embodiments, the holding period of successive holding temperatures may be different. For example, a rock sample may have a first holding period of five minutes, a second holding period of three minutes and a third holding period of four minutes. Other examples include a first holding period of three minutes, a second holding period of seven minutes, and a third holding period of six minutes. FIG. 2-7 illustrate sample temperature profiles of the current invention, including variable temperature increases and holding periods.

Referring back to FIG. 2, the rock sample may be held at seven holding temperatures 220, 222, 224, 226, 228, 230, 232 for a holding period of five minutes each. The difference between the base temperature 234 and the first holding temperature 220 may be 25°. The difference in temperature between the next five successive pairs of holding temperatures 220 to 222, 222 to 224, 224 to 226, 226 to 228, and 228 to 230 may be the same at 50° C. The difference in temperature between the sixth holding temperature 230 and the seventh holding temperature 232 may be 350° C. It should be noted that the information collected while holding the rock sample at the first six holding temperatures 220, 222, 224, 226, 228, 230 may help to define the S1 parameter, while the information collected at the seventh holding temperature may help define the S2 parameter.

The rate of temperature increase between the base temperature 234 and the first holding temperature 220, as well as between the next five successive pairs of holding temperatures 220 to 222, 222 to 224, 224 to 226, 226 to 228, and 228 to 230 may be 200° C. per minute. However, each change in holding temperature need not have the same rate of temperature increase; the rate of temperature increase between the sixth holding temperature 230 and the seventh holding temperature 232 may be 50° C. per minute.

Figure 3:
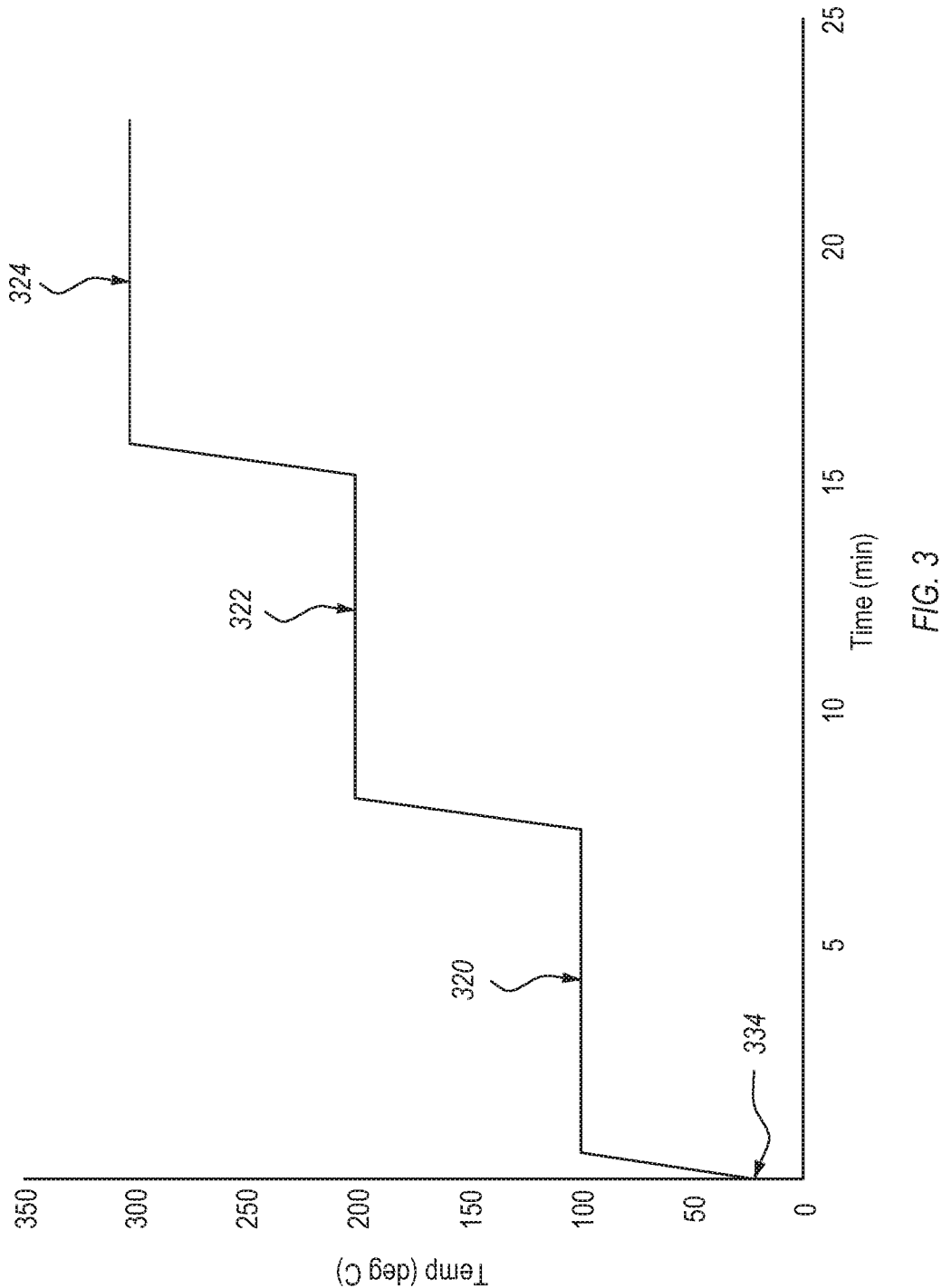
FIG. 3 illustrates another example temperature profile.

In one embodiment, and as depicted in FIG. 3, a rock sample is held at three holding temperatures 320, 322, 324 for a holding period of seven minutes each. A first temperature difference between the base temperature 334 and the first holding temperature 320 is about 75° C. A second difference in temperature between the first holding temperature 320 and the second holding temperature 322 is about 100° C. A third difference in temperature between the second holding temperature 322 and the third holding temperature 324 is about 100° C.

Figure 4:
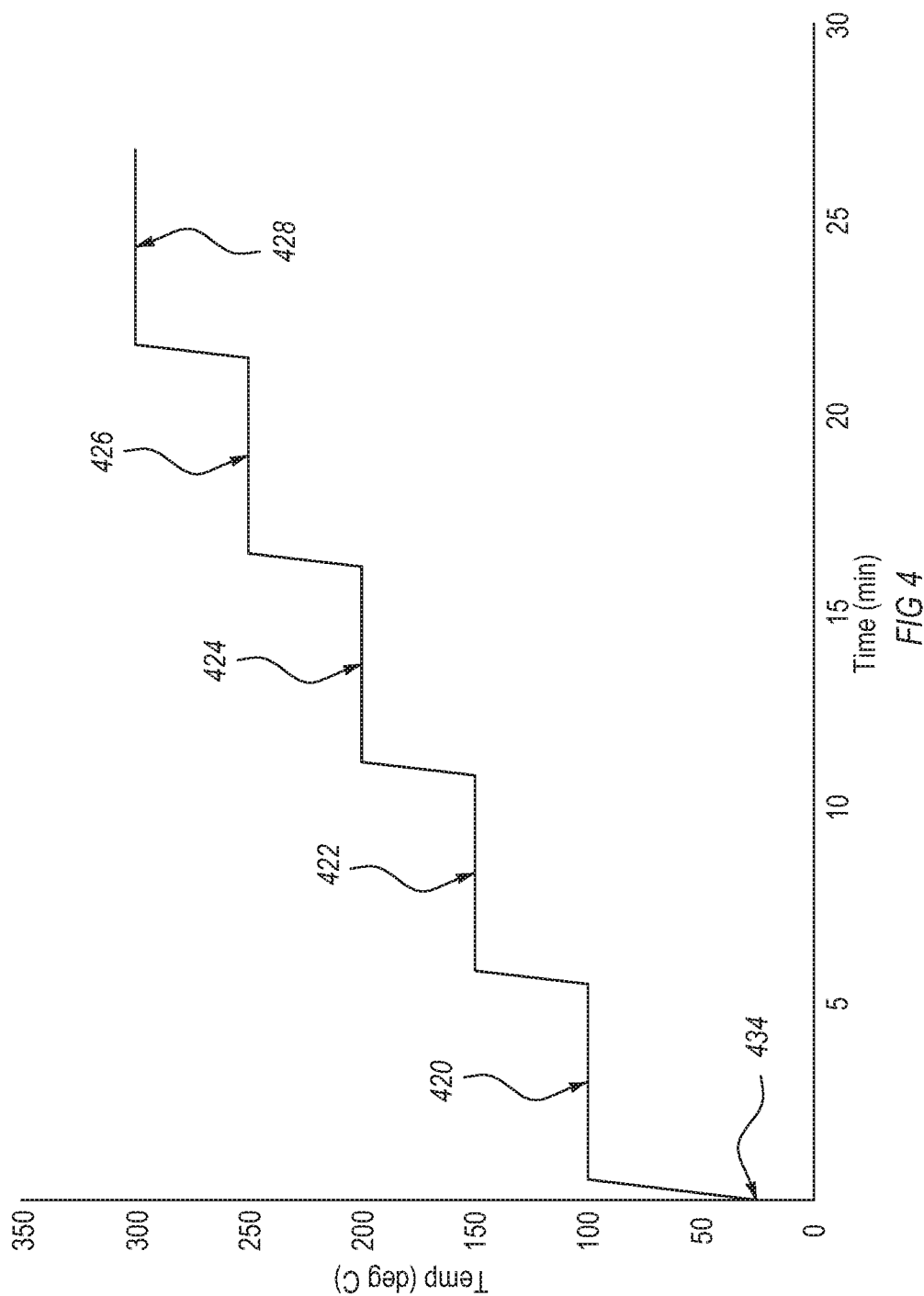
FIG. 4 illustrates yet another example temperature profile.

In another embodiment, and as depicted in FIG. 4, the rock sample may be held at five holding temperatures, 420, 422, 424, 426, 428 for a holding period of five minutes each. A first difference between the base temperature 434 and the first temperature 420 is about 75° C. The difference in temperature between the next four successive pairs of holding temperatures 420 to 422, 422 to 424, 424 to 426, and 426 to 428 is about the same at 50° C.

Figure 5:
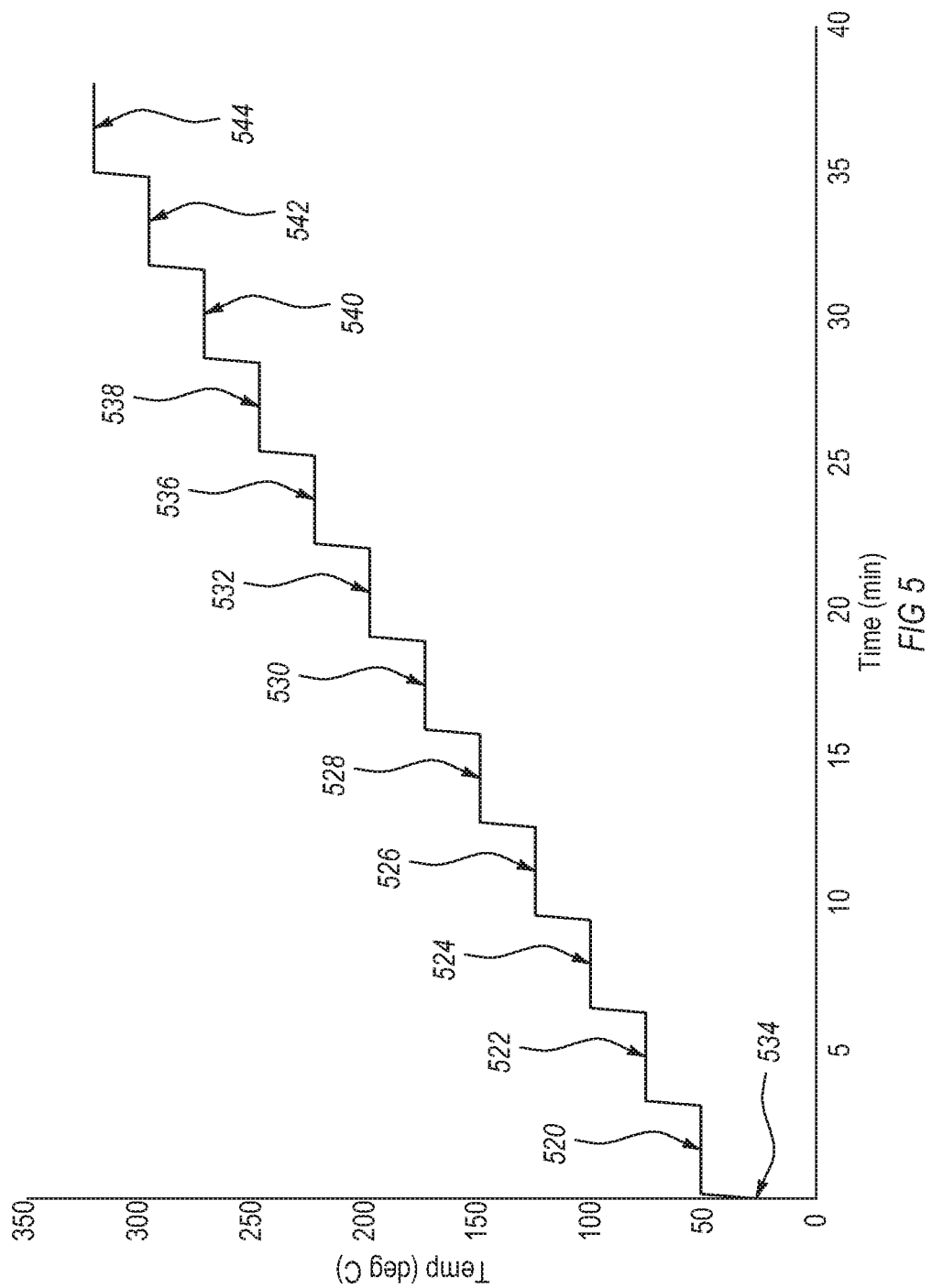
FIG. 5 illustrates a further example temperature profile.

In an additional embodiment, and as depicted in FIG. 5, the rock sample is held at twelve holding temperatures, 520, 522, 524, 526, 528, 530, 532, 536, 538, 540, 542, 544 for a holding period of three minutes each. The difference in temperature between successive holding temperatures is about 25° C.

Figure 6:
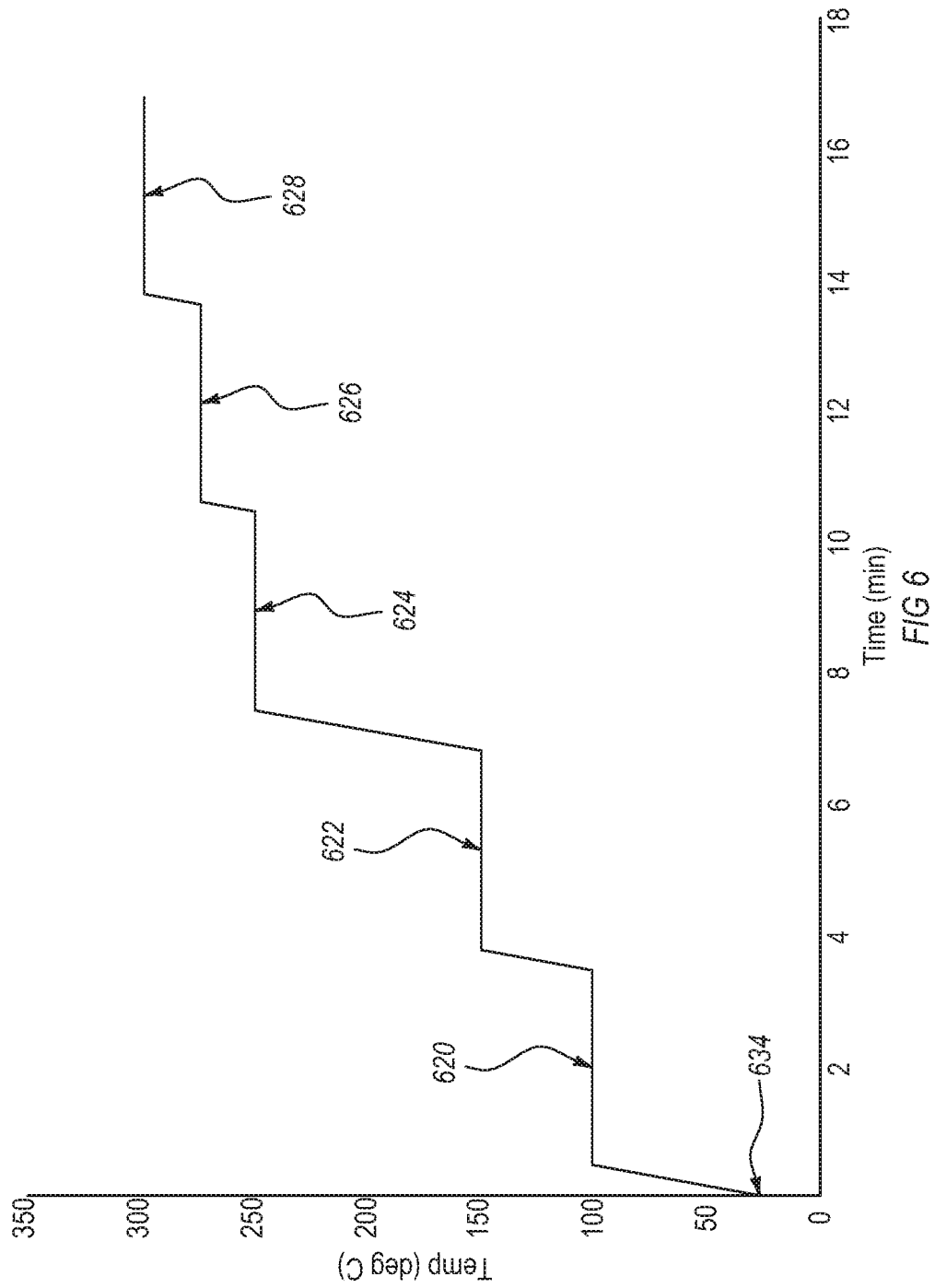
FIG. 6 illustrates a yet further example temperature profile.

Referring to FIG. 6, other embodiments may include a rock sample being heated to five holding temperatures 620, 622, 624, 626, 628 for a holding period of three minutes each. A first difference in temperature between the base temperature 634 and the first holding temperature 620 may be about 75° C. A second difference in temperature between the first holding temperature 620 and the second holding temperature 622 may be about 50° C. A third difference in temperature between the second holding temperature 622 and the third holding temperature 624 may be about 100° C. A fourth difference in temperature between the third holding temperature 624 and the fourth holding temperature 626 may be about 25° C. A fifth difference in temperature between the fourth holding temperature 626 and the fifth holding temperature 628 may be about 25° C.

Figure 7:
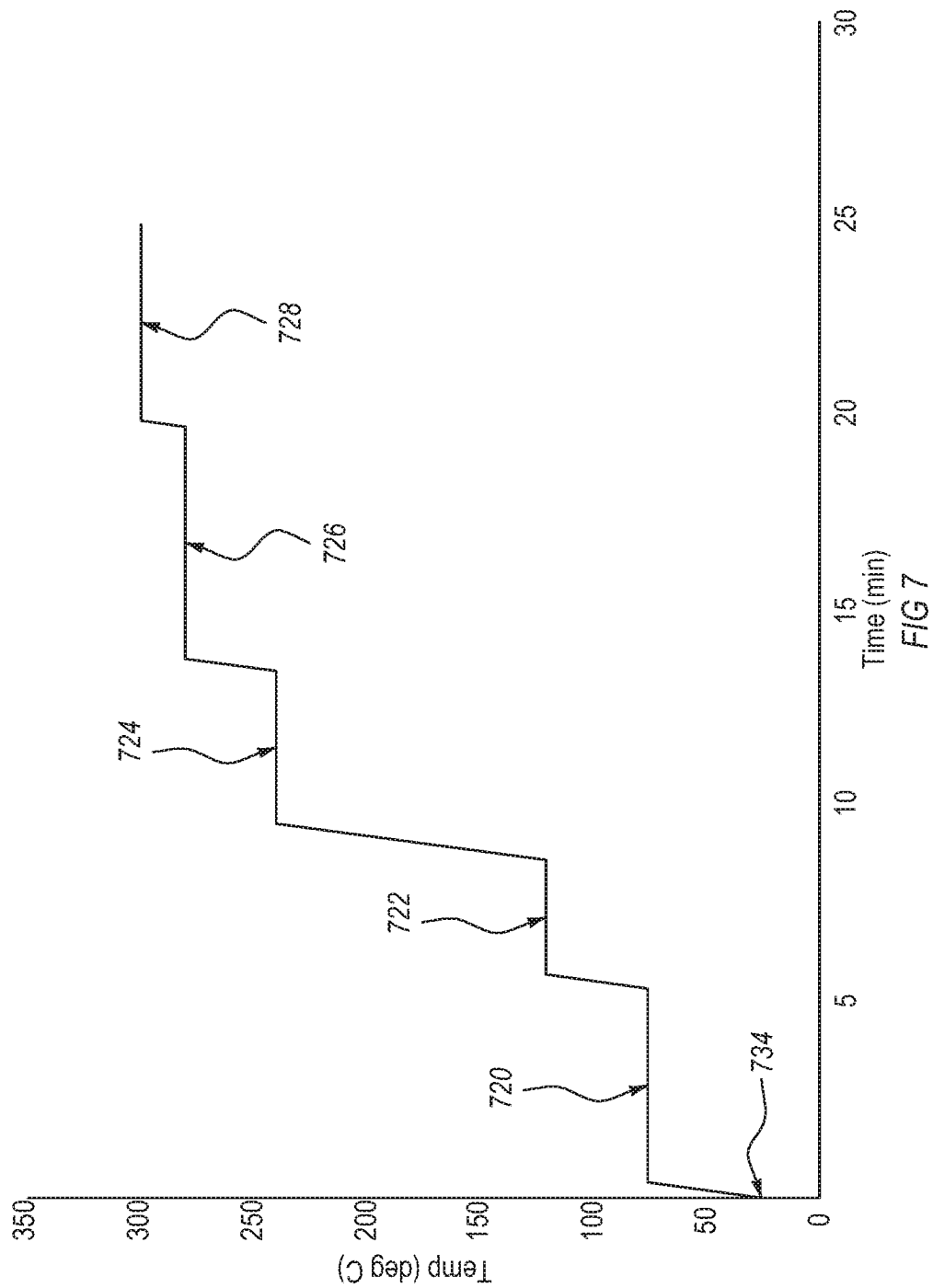
FIG. 7 illustrates a still further example temperature profile.

Referring to FIG. 7, in some embodiments, a rock sample may be heated to five holding temperatures, 720, 722, 724, 726, 728. A first difference in temperature between the base temperature 734 and the first holding temperature 720 may be about 50° C., and the rock sample may be held at the first holding temperature 720 for a first holding period of five minutes. A second difference in temperature between the first holding temperature 720 and the second holding temperature 722 may be about 45° C., and the rock sample may be held at the second holding temperature 722 for a second holding period of three minutes. A third difference in temperature between the second holding temperature 722 and the third holding temperature 724 may be about 120° C., and the rock sample may be held at the third holding temperature 724 for a third holding period of four minutes. A fourth difference in temperature between the third holding temperature 724 and the fourth holding temperature 726 may be about 40° C., and the rock sample may be held at the fourth holding temperature 726 for a fourth holding period of six minutes. A fifth difference in temperature between the fourth holding temperature 726 and the fifth holding temperature 728 may be about 20° C., and the rock sample may be held at the fifth holding temperature 728 for a fifth holding period of five minutes.

As illustrated by FIGS. 2-7, it should be appreciated that the number and timing of holding periods can vary between methods. Further, the number and timing of holding periods can vary within a method. Additionally, or alternatively, the successive and relative increase in temperature between holding periods can be the same or it can be different, as clearly illustrated by the figures. By collecting data at different temperatures and for different periods of time, hydrocarbons within a rock sample can be better characterized, thereby allowing for a more accurate determination of the rock sample composition. By analyzing a rock sample using FTIR at a first time point and a final time point with intervening data collection points at successively increasing temperatures, implementations of the present disclosure enable assessment of one or more of: source rock maturity, the amount or concentration of free petroleum, the composition of the free petroleum, the water and/or oil saturation, the hydrocarbon pore volume PVT properties of free petroleum/oil, porosity, permeability, gas to oil ratio, bubble point, due point, and/or viscosity of oil within the rock sample. Advantageously, these parameters can be derived in a closed system, as opposed to the typical open system, and can be empirically measured from a real sample instead of being inferred from indirect measurements.

As such, the data derived from embodiments of the present disclosure can be used in concert with traditional logging techniques to yield empirical relationships between mineralogy, maceral content, in fluid content to provide a closed system interior balance of the studied formations. The systems and methods disclosed herein can be applied to the exploration and development of oil and gas. In exploration, the disclosed systems and methods can be used to characterize regional trends and sweet spots within reservoirs. In development, the disclosed systems and methods can be used for reservoir characterization, fluid characterization, reservoir management, well spacing, and development decisions (e.g., hydraulic fracture spacing).

Additionally, by taking measurements of certain gases that are given off by the gradual heating process in any of the temperature programs disclosed herein, the API gravity of petroleum in a given sample can be determined. The API gravity of a given rock sample provides a direct relationship to the amount and quality of crude oil that can be yielded from a given location. The less dense given oil is, the easier it will be to refine. Traditionally, API gravity is measured in fluids produced from a well or reservoir. The embodiments disclosed herein extends this measurement to oils still reservoired in rocks and enables more accurate and available testing of petroleum quality for oil exploration and acquisition. Implementations of the present disclosure provide alternative methods to the testing of prospective drilling in petroleum system sites and can be done comparatively quickly and inexpensively (e.g., within 30 minutes). Current industry methods require the drilling out of an earth sample, extracting oil from the sample, and then determining the API gravity of the extracted oil. If limitations of the present disclosure allow for an API gravity determination directly from a rock sample and without purifying or extracting oil from the sample as done in traditional methods.

Embodiments described herein may be implemented on various types of computing systems. These computing systems are now increasingly taking a wide variety of forms. Computing systems may, for example, be handheld devices, appliances, laptop computers, desktop computers, mainframes, distributed computing systems, or even devices that have not conventionally been considered a computing system. In this description and in the claims, the term "computing system" is defined broadly as including any device or system (or combination thereof) that includes at least one physical and tangible processor, and a physical and tangible memory capable of having thereon computer-executable instructions that may be executed by the processor. A computing system may be distributed over a network environment and may include multiple constituent computing systems.

As used herein, the term "executable instructions" or "executable component" can refer to software objects, routings, or methods that may be executed on the computing system. The different components, modules, engines, and services described herein may be implemented as objects or processes that execute on the computing system (e.g., as separate threads). Embodiments of the methods described herein may be described with reference to acts that may be performed by one or more computing systems. If such acts are implemented in software, one or more processors of the associated computing system that performs the act direct the operation of the computing system in response to having executed computer-executable instructions.

Figure 8:
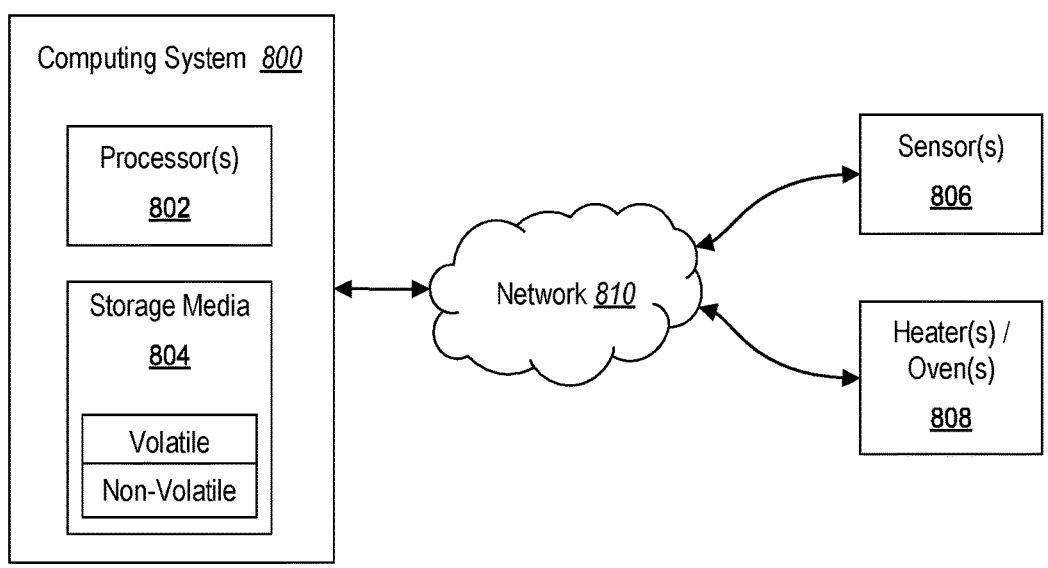
FIG. 8 illustrates an exemplary computer system for implementing one or more methods disclosed herein, including, for example, the method outlined in FIG. 1.

Referring now to FIG. 8, the methods described above may be implemented using a computer system 800 to control one or more heaters or ovens 808 and sensors 806. Computer executable instructions may be stored on a physical non-transitory computer readable storage media 804. The computer executable instructions may be executed by one or more processors 802, the processors, in turn, causing the computing system 800 to control the physical elements necessary to implement the method (e.g., the heaters, ovens, sensors, etc.).

In some embodiments, a temperature profile (e.g., such as those illustrated in FIGS. 2-7 or otherwise disclosed herein), include a series of holding temperatures, holding periods, and rates of temperature increase. Each of the foregoing may be stored in storage media 804 individually or as part of a temperature profile to be executed. Instructions for an oven to increase temperature according to the temperature profile may also be stored in the storage media 804, and executed by the one or more processors 802. The one or more processors 802 may then cause a computer system to change the oven's temperature according to the temperature profile.

In other embodiments, instructions for the operation of one or more sensors may be included in the storage media 804 and implemented by the processor 802. The one or more sensors 806 may include an FTIR sensor, a gas chromatograph, a mass spectrometer, and a pyrolysis machine. In at least on embodiment, the one or more processors 802 may then cause a computer system to operate the one or more sensors 806 in coordination with a specific temperature profile. The data collected by the one or more sensors may then be stored on the storage media 804.

In some embodiments, instructions for analyzing the data collected from the one or more sensors 806 may be included in the storage media 804 and implemented by the one or more processors 802. The data collected from the one or more sensors may be used to calculate API gravity, the S1 parameter, the S2 parameter, and/or other parameters useful to the analysis of rock samples. In other embodiments, the data collected from the one or more sensors 806 may be exported in a data file, for analysis and use by a user.

It should be appreciated that the computing system 800 and one or more of the sensors 806 and ovens 808 can be part of or controlled by the same system. Alternatively, computing system 800 can be communicatively coupled to the sensors 806 and/or ovens 808 via a network 810. Accordingly, in some embodiments, a user can analyze rock samples at a location remote from one or more of the sensors 806 and/or ovens 808 using a computing system 800.

Embodiments described herein also include physical and other computer-readable media for carrying or storing computer-executable instructions and/or data structures. Such computer-readable media can be any available media that can be accessed by a general-purpose or special-purpose computer system. Computer-readable media that store computer-executable instructions and/or data structures are computer storage media. Computer-readable media that carry computer-executable instructions and/or data structures are transmission media. Thus, by way of example, and not limitation, embodiments described herein can comprise at least two distinctly different kinds of computer-readable media: computer storage media and transmission media.

Computer storage media are physical hardware storage media that store computer-executable instructions and/or data structures. Physical hardware storage media include computer hardware, such as RAM, ROM, EEPROM, solid state drives ("SSDs"), flash memory, phase-change memory ("PCM"), optical disk storage, magnetic disk storage or other magnetic storage devices, or any other hardware storage device(s) which can be used to store program code in the form of computer-executable instructions or data structures, which can be accessed and executed by a general-purpose or special-purpose computer system to implement the functionality disclosed herein.

Transmission media can include a network and/or data links which can be used to carry program code in the form of computer-executable instructions or data structures, and which can be accessed by a general-purpose or special-purpose computer system. A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer system, the computer system may view the connection as transmission media. Combinations of the above should also be included within the scope of computer-readable media.

Further, upon reaching various computer system components, program code in the form of computer-executable instructions or data structures can be transferred automatically from transmission media to computer storage media (or vice versa). For example, computer-executable instructions or data structures received over a network or data link can be buffered in RAM within a network interface module (e.g., a "NIC"), and then eventually transferred to computer system RAM and/or to less volatile computer storage media at a computer system. Thus, it should be understood that computer storage media can be included in computer system components that also (or even primarily) utilize transmission media.

Computer-executable instructions comprise, for example, instructions and data which, when executed at one or more processors, cause a general-purpose computer system, special-purpose computer system, or special-purpose processing device to perform a certain function or group of functions. Computer-executable instructions may be, for example, binaries, intermediate format instructions such as assembly language, or even source code.

As used herein, the terms "approximately," "about," and "substantially" as used herein represent an amount close to the stated amount that still performs a desired function or achieves a desired result. For example, the terms "approximately," "about," and "substantially" may refer to an amount that is within less than 5% of, within less than 1% of, within less than 0.1% of, and within less than 0.01% of a stated amount.

The present invention may be embodied in other specific forms without departing from its spirit or characteristics. The described embodiments are to be considered in all respects only as illustrative and not restrictive. Accordingly, the scope of the invention, as disclosed, includes any and all combinations of the disclosed features and embodiments.

The scope of the invention is, as claimed, indicated by the appended claims rather than by the foregoing description. All changes which come within the meaning and range of equivalency of the claims are to be embraced within their scope.

What is claimed is:

1. A method for analyzing a free petroleum content reservoired within a rock sample to enable a more accurate and available testing of petroleum quality for oil exploration and acquisition, comprising:
   heating the rock sample from a base temperature of about ambient or room temperature to a first holding temperature, the first holding temperature being less than 350° C.;
   holding the rock sample at the first holding temperature for a first holding period;
   heating the rock sample to a second holding temperature, the second holding temperature being greater than the first holding temperature;
   holding the rock sample at the second holding temperature for a second holding period;
   heating the rock sample to a third holding temperature, the third holding temperature being greater than the second holding temperature and no more than 350° C.;
   holding the rock sample at the third holding temperature for a third holding period;
   collecting data on properties of gases released from the rock sample during the first holding period, the second holding period and the third holding period through at least one of pyrolysis, gas chromatography, or mass spectrometry; and
   determining the free petroleum content of the rock sample based on the collected data, the determined free petroleum content of the rock sample enabling a more accurate and available testing of petroleum quality for oil exploration and acquisition.

2. The method of claim 1, the method further comprising analyzing the rock sample using Fourier transform infrared spectroscopy prior to heating the rock sample from the base temperature to the first holding temperature and after the third holding period.

3. The method of claim 1, wherein the rock sample has a free hydrocarbon content, and the third holding temperature corresponds with a temperature required to determine the free hydrocarbon content.

4. The method of claim 1, wherein holding the rock sample at the first holding temperature, holding the rock sample at the second holding temperature, and holding the rock sample at the third holding temperature includes holding a temperature of the rock sample within plus or minus 1° C. during the first holding period, the second holding period and the third holding period, respectively.

5. The method of claim 1, wherein a first difference in temperature between the base temperature and the first holding temperature, a second difference in temperature between the first holding temperature and the second holding temperature, and a third difference in temperature between the second holding temperature and the third holding temperature are about the same.

6. The method of claim 1, wherein a first difference in temperature between the base temperature and the first holding temperature, a second difference in temperature between the first holding temperature and the second holding temperature, and a third difference in temperature between the second holding temperature and the third holding temperature are each at least 10° C.

7. The method of claim 1, wherein the heating of the rock sample from the base temperature to the first holding temperature, heating of the rock sample from the first holding temperature to the second holding temperature, and heating of the rock sample the second holding temperature to the third holding temperature occurs at a rate of between 50° C. and 200° C. per minute.

8. The method of claim 1, wherein the first holding period, the second holding period, and the third holding period are between three and seven minutes.

9. The method of claim 1, wherein the first holding period, the second holding period, and the third holding period are the same.

10. The method of claim 1, wherein the rock sample is heated in a closed system.

11. The method of claim 1, wherein the rock sample is heated in an inert environment.

12. A method for analyzing a free petroleum content reservoired within a rock sample to enable a more accurate and available testing of petroleum quality for oil exploration and acquisition, comprising:
   analyzing the rock sample using Fourier transform infrared spectroscopy;
   heating the rock sample from a base temperature of about ambient or room temperature to a first holding temperature less than 350° C. after analyzing the rock sample using Fourier transform infrared spectroscopy;
   holding the rock sample at the first holding temperature for a first holding period;
   heating the rock sample to a second holding temperature, the second holding temperature being greater than the first holding temperature;
   holding the rock sample at the second holding temperature for a second holding period;
   heating the rock sample to a third holding temperature, the third holding temperature being greater than the second holding temperature and no more than 350° C.;
   holding the rock sample at the third holding temperature for a third holding period;
   collecting data on properties of gases released from the rock sample during the first holding period, the second holding period, and the third holding period through at least one of pyrolysis, gas chromatography, and mass spectrometry;
   analyzing the rock sample using Fourier transform infrared spectroscopy after the third holding period and while the rock sample is at a temperature no more than 350° C.;
   heating the rock sample to a fourth holding temperature, the fourth holding temperature being greater than the third holding temperature and no more than 800° C.; and
   determining the free petroleum content of the rock sample based at least on data collected from the properties of gases released from the rock sample during the first holding period, the second holding period, and the third holding period, from analyzing the rock sample using Fourier transform infrared spectroscopy prior to heating the rock from the base temperature to the first holding temperature, and from analyzing the rock sample using Fourier transform infrared spectroscopy after the third holding period,
   wherein the determined free petroleum content of the rock sample enables a more accurate and available testing of petroleum quality for oil exploration and acquisition.

13. The method of claim 12, wherein the fourth holding temperature corresponds to the temperature at which hydrocarbons stop decomposing.

14. The method of claim 12, wherein holding the rock sample at the first holding temperature, holding the rock sample at the second holding temperature, and holding the rock sample at the third holding temperature includes holding a temperature of the rock sample of plus or minus 1° C. during the first holding period, the second holding period and the third holding period, respectively.

15. The method of claim 12, wherein a first difference in temperature between the base temperature and the first holding temperature, a second difference in temperature between the first holding temperature and the second holding temperature, and a third difference in temperature between the second holding temperature and the third holding temperature are about the same.

16. The method of claim 12, wherein the first holding period, the second holding period, and the third holding period have a duration between three and seven minutes.

17. A computing system comprising:
   one or more processors; and
   one or more computer readable media having stored thereon computer-executable instructions that when executed by the one or more processors configure the computing system to perform at least the following:
      receive data from an analysis of the rock sample using Fourier transform infrared spectroscopy;
      subsequent to receiving data from the analysis of the rock sample using Fourier transform infrared spectroscopy, receive one or more properties of one or more gases released from the rock sample during a first holding period, a second holding period, and a third holding period through at least one of pyrolysis, gas chromatography, and mass spectrometry,
      wherein prior to the first holding period, the rock sample is heated from a base temperature to a first holding temperature, the first holding temperature being greater than the base temperature,
      wherein subsequent to the first holding period and prior to the second holding period, the rock sample is heated to a second holding temperature, the second holding temperature being greater than the first holding temperature, and
      wherein subsequent to the second holding period and prior to the third holding period, the rock sample is heated to a third holding temperature, the third holding temperature being greater than the second holding temperature and no more than 350° C.;
      receive data from a subsequent analysis of the rock sample using Fourier transform infrared spectroscopy, subsequent to the third holding period; and
      determine the free petroleum content of the rock sample based on the collected data, the determined free petroleum content of the rock sample enabling a more accurate and available testing of petroleum quality for oil exploration and acquisition.

18. The method of claim 17, further comprising computer-executable instructions that are executable by the one or more processors to cause the computing system to cause a heater or oven to heat the rock sample from the base temperature to the first holding temperature for the first holding period, heat the rock sample to the second holding temperature for the second holding period, and heat the rock sample to the third holding temperature for the third holding period.

19. The method of claim 17, further comprising computer-executable instructions that are executable by the one or more processors to cause the computing system to calculate an API gravity of the rock sample based on the data from the analysis, the one or more properties of the one or more gases, and the data from the subsequent analysis.

* * * * *